(12) United States Patent
Vettukattil et al.

(10) Patent No.: US 11,839,526 B2
(45) Date of Patent: Dec. 12, 2023

(54) FLOW REGULATING DEVICE IN THE HEART

(71) Applicant: Occlutech GmbH, Schaffhausen (CH)

(72) Inventors: Joseph John Vettukattil, Grand Rapids, MI (US); Mehmet Hakan Akpinar, Istanbul (TR)

(73) Assignee: Occlutech GmbH, Schaffhausen (CH)

( * ) Notice: Subject to any disclaimer, the term of this patent is extended or adjusted under 35 U.S.C. 154(b) by 937 days.

(21) Appl. No.: 16/805,440

(22) Filed: Feb. 28, 2020

(65) Prior Publication Data

US 2020/0268515 A1 Aug. 27, 2020

Related U.S. Application Data

(63) Continuation of application No. 15/508,473, filed as application No. PCT/EP2015/070659 on Sep. 9, 2015, now Pat. No. 10,595,999.

(Continued)

(51) Int. Cl.
*A61B 17/00* (2006.01)
*A61M 27/00* (2006.01)
(Continued)

(52) U.S. Cl.
CPC ........ *A61F 2/2493* (2013.01); *A61B 17/0057* (2013.01); *A61F 2/0077* (2013.01);
(Continued)

(58) Field of Classification Search
CPC ...... A61B 17/0057; A61B 2017/00575; A61B 2017/00592; A61B 2017/00597;
(Continued)

(56) References Cited

U.S. PATENT DOCUMENTS 6,007,544 A 12/1999 Kim
6,123,715 A 9/2000 Amplatz
(Continued)

FOREIGN PATENT DOCUMENTS

CN 103945774 A 7/2014
CN 104274262 A 1/2015
(Continued)

OTHER PUBLICATIONS

European Patent Office, Notice of Opposition dated Jun. 10, 2022 in European Patent Application No. 18189043.5, 57 pages.
(Continued)

*Primary Examiner* — Leslie R Deak
(74) *Attorney, Agent, or Firm* — Inskeep IP Group, Inc.

(57) ABSTRACT

A blood flow regulator for creating a shunt in the heart, comprising; a proximal element having a general disc-shape, defined by a braid of one or more wires extending about a central aperture of the proximal element; a distal element having a general disc-shape, defined by a braid of one or more wires extending about a central aperture of the distal element; and a third element defining a neck section intermediate the proximal and distal elements and forming a cavity having a diameter no greater than a diameter of each of the distal and proximal elements, wherein said distal element comprises at least one loop of a wire extending radially outwardly from a center of the distal element and returning towards said center of said distal element.

14 Claims, 11 Drawing Sheets

Related U.S. Application Data

(60) Provisional application No. 62/077,680, filed on Nov. 10, 2014, provisional application No. 62/047,843, filed on Sep. 9, 2014.

(51) Int. Cl.
*A61F 2/24* (2006.01)
*A61F 2/00* (2006.01)

(52) U.S. Cl.
CPC . *A61M 27/002* (2013.01); *A61B 2017/00247* (2013.01); *A61B 2017/00575* (2013.01); *A61B 2017/00592* (2013.01); *A61B 2017/00597* (2013.01); *A61B 2017/00606* (2013.01); *A61B 2017/00623* (2013.01); *A61F 2002/0086* (2013.01); *A61F 2210/0004* (2013.01); *A61F 2210/0014* (2013.01); *A61F 2210/0076* (2013.01); *A61F 2230/0008* (2013.01); *A61F 2230/0071* (2013.01); *A61F 2230/0095* (2013.01); *A61F 2240/001* (2013.01); *A61F 2250/0048* (2013.01)

(58) Field of Classification Search
CPC . A61B 2017/00606; A61B 2017/00623; A61F 2002/0086; A61F 2210/0004; A61F 2210/0014; A61F 2210/0076; A61F 2250/0048; A61M 27/002
See application file for complete search history.

(56) References Cited

U.S. PATENT DOCUMENTS

| | | |
|---|---|---|
| 2002/0099437 A1 | 7/2002 | Anson et al. |
| 2003/0057156 A1 | 3/2003 | Peterson et al. |
| 2005/0165344 A1 | 7/2005 | Dobak, III |
| 2006/0224183 A1 | 10/2006 | Freudenthal |
| 2009/0082803 A1 | 3/2009 | Adams et al. |
| 2009/0198315 A1 | 8/2009 | Boudjemline |
| 2012/0172927 A1 | 7/2012 | Campbell et al. |
| 2014/0194921 A1 | 7/2014 | Akipinar |

FOREIGN PATENT DOCUMENTS

| | | | |
|---|---|---|---|
| EP | 1849440 | A1 | 10/2007 |
| EP | 1480708 | B1 | 8/2009 |
| JP | 2003527939 | A | 9/2003 |
| WO | WO2001/072367 | A1 | 10/2001 |
| WO | WO2007/083288 | A2 | 7/2007 |
| WO | WO2013/041721 | A1 | 3/2013 |

OTHER PUBLICATIONS

Patent Assignment 044334/0646 containing information and documents relating to the counterpart U.S. Patent derived from PCT/EP2015/070659EP, *USPTO*, date recorded Dec. 7, 2017, 12 pages.
Patel, Mehul B. et al., "Implantable Atrial Flow Regulator for Severe, Irreversible Pulmonary Arterial Hypertension," *EuroIntervention 2015*, 11:706-709, https://occlutech.com/2015-patel-eurointervention/, published online ahead of print Jul. 2015, 25 pages.
Engelmayr, Jr., George C. et al., "A Novel Flex-Stretch-Flow Bioreactor for the Study of Engineered Heart Valve Tissue Mechanobiology", *NIH Public Access*, Ann Biomed Eng. May 2008; 36(5): 700-712. doi: 10.1007/s10439-008-9447-6, available in PMC Jul. 3, 2013, 22 pages.
Engelmayr, Jr., George C. et al., "Cyclic flexure and laminar flow synergistically accelerate mesenchymal stem cell-mediated engineered tissue information: Implications for engineered heart valve tissues", *Elsevier Ltd.*, Biomaterials 27 (2006) 6083-6095, available online Aug. 23, 2006, www.elsevier.com/locate/biomaterials, 13 pages.
WIPO, International Preliminary Examining Authority (European Patent Office), International Preliminary Report on Patentability dated Aug. 3, 2016 in International Patent Application No. PCT/EP2015/070659, 12 pages.
WIPO, European International Search Authority, International Search Report and Written Opinion dated Nov. 3, 2015 in International Patent Application No. PCT/EP2015/070659, 9 pages.

FLOW REGULATING DEVICE IN THE HEART

RELATED APPLICATIONS

This application is a continuation of U.S. patent application Ser. No. 15/508,473, filed Mar. 2, 2017, entitled A Flow Regulating Device In The Heart, which is the National Phase of and claims priority to International Patent Application No. PCT/EP2015/070659 International Filing Date Sep. 9, 2015, entitled A Flow Regulating Device In The Heart; which claims benefit of U.S. Provisional Application Ser. No. 62/047,843 filed Sep. 9, 2014 entitled A Flow Regulating Device In The Heart; and U.S. Provisional Application Ser. No. 62/077,680 filed Nov. 10, 2014 entitled A Flow Regulating Device In The Heart; all of which are incorporated herein by reference in their entireties

FIELD OF THE INVENTION

This disclosure pertains in general to the field of medical implants. More particularly, the disclosure relates to a device suitable for implantation in the atrial septum in the heart of a mammal. The device providing a precise dimension for an opening in the septum, with a predetermined diameter, where the device remains open for a predetermined period of time, and serving to control flow rate across the septum.

BACKGROUND OF THE INVENTION

In a healthy heart which is composed of four chambers, atria collect the blood from body and the lungs, and the ventricles pump the blood to the lungs and the body. The oxygenated blood which is pumped by the left ventricles carries oxygen to the body. Deoxygenated blood is returned to the right heart via veins and pumped to the lungs via pulmonary artery originated from the right heart. The oxygenated blood in the lungs flows into the left atrium via pulmonary veins and then to the left ventricle where it is pumped to the body. Right and left chambers of the heart are separated by a wall to avoid the mixture of oxygenated and deoxygenated blood. Congenital opening between right and left atria of the heart is called as ASD (atrial septal defect). In the presence of an ASD, oxygenated blood in the left atrium flows into the right atrium, and the amount of the blood to be pumped by the right atria increases. In time, this would lead to overload, hypertension in the pulmonary arteries (pulmonary hypertension) and heart failure, decreasing life expectancy. Moreover, the emboli passing through this hole may reach to the brain leading to strokes. If the blood flowing through the left atrium to the right atrium is above a certain amount, ASD must be occluded. Otherwise, irreversible damage may occur in the pulmonary arteries.

In the fetal heart, there is a hole (foramen ovale) between the atria, and this hole is partially covered by a membrane. This hole between the membrane allows the blood to pass from right to left atria, and it is vital for the baby. Following the birth, the membrane closes the hole, and in few months the hole is completely occluded in most cases.

The Atrial Flow Regulator (AFR) or the blood flow regulating device, as referred to as below, is intended to create a hole (small ASD) between the two collecting chambers in the heart (right and Left Atria), i.e. opposite to the purpose of an occluder. This will allow flow of blood from a chamber that is stiff and under high pressure to a chamber that is less stiff and under lesser pressure. By creating such a hole, symptoms resulting from back flow of blood into the areas filling that chamber could be prevented. For example, if the pressure in the left atria (LA) is high then the back pressure would be into the lungs from which the oxygenated blood is draining into the LA. This causes the patient to be breathless and give symptoms like coughing and an inability to lie flat or climb stairs. Creating a hole in the atrial septum will decompress the LA into a less-stiff and low pressure Right Atrium (RA). This would help the patient to be free of such symptoms. Similarly, if the Right Atrium (RA) is under high pressure or becomes stiff from a failing Right Ventricle (RV), the chamber can be decompressed by a hole created in the atrial septum. This will reduce symptoms from high pressure in the veins draining into the RA like liver veins, kidney veins, veins from the intestine, etc.

When such a hole is created, it should be calibrated so as to control the amount of pressure drop and amount of blood flowing through the hole. When blood flows from the RA to LA, the patients may become bluer but will have better blood flow into the vital organs. If the blood flow is from LA to the RA then there is no problem with saturations but there may be a slight reduction in blood flow into the organs during more than moderate exercise which otherwise would have been not possible in those patients.

Although rare, there are some risks during the transcatheter procedure. While attempting to make a hole to implant the AFR, laceration or bleeding may occur in vessels which may require surgical invention or blood transfusion. Infection is another risk following the procedure, which may require antibiotic treatment. Very rarely stroke and accordingly long term function loss may occur. Allergic reactions or loss of renal functions may develop due to contrast material. Creating a hole may also predispose the patient to paradoxic embolism and stroke if the blood flows from right to left.

Urgent surgical intervention may be needed due to inappropriate location of the AFR device or premature release of the device form the catheter. The device can be dislocated after being released and it may harm the adjacent heart valves. This situation may require operation. Rarely, the device may not be implantable or clots can form around the device, leading to embolism.

Sivaprakasam M, Kiesewetter C, Veldtman G R, Salmon A P, Vettukattil J. published an article "New technique for fenestration of the interatrial septum" j intery cardiol In 2006 August 19(4):334-6. This was created by improvised use of a stent not intended for this use. However, it is important to ensure that the defect created in the heart is a precise diameter to a calibrated size to allow appropriate amount of blood flow, just enough to maintain the necessary cardiac output without causing other complications like severe decrease in oxygenation, device dislodgement, decrease in the size of hole in the device etc. It is equally important that such devices are precisely positioned to avoid damage or dysfunction of healthy heart tissues or structures.

Prior devices for creating a shunt or an opening in the heart have a middle section, which can be called the conjoined ring, which is circular and provides most of the support to the right and left disc-shaped end sections in order to keep its circular shape and calibrated diameter, and to keep its shape memory. Such a device can be placed between two cardiac chambers. To allow pressure reduction between the two cardiac chambers, a manual hole is made by splaying the wires of the device. A problem with previous devices is lack of stability and thereby difficulties in attaining a well-defined calibrated opening. Moreover, with conventional devices, due to the hole being in the ring that latches on to the wall or septum (partition between the two chambers), the hole may get covered in the process of endothelialisation, i.e. the natural process of the body to cover any foreign material. A further problem with prior art device is the disruption of the endothelialization process, which can cause formation of embolies travelling in the blood stream.

Thus with prior art device there is a challenge to achieve sufficient stability, a sufficiently well-defined shunt, and reduced risk of formation of embolies.

Thus, it would be advantageous to provide an improved blood flow regulating device with improved stability, allowing for improved support, and the ability to retain the calibrated size, and improved properties with respect to endothelialization, as well as a method of manufacturing such device.

SUMMARY OF THE INVENTION

Accordingly, embodiments of the present disclosure preferably seek to mitigate, alleviate or eliminate one or more deficiencies, disadvantages or issues in the art, such as the above-identified, singly or in any combination by providing an AFR device or blood flow regulating device according to the appended patent claims.

According to a first aspect of the disclosure a blood flow regulator for creating a shunt in the heart is disclosed comprising a proximal element having a general disc-shape, defined by a braid of one or more wires extending about a central aperture of the proximal element, a distal element having a general disc-shape, defined by a braid of one or more wires extending about a central aperture of the distal element, and a third element defining a neck section intermediate the proximal and distal elements and forming a cavity having a diameter no greater than a diameter of each of the distal and proximal elements. The distal element comprises at least one loop of a wire extending radially outwardly from a center of the distal element and returning towards said center of the distal element.

According to a second aspect of the disclosure a method of manufacturing a blood flow regulator is disclosed comprising braiding a tubular braid of wires, where opposite ends of each wire are arranged at a proximal portion of the tubular braid, and loops of the wires are arranged at a distal end of the tubular braiding. The method comprising forming a distal disc of the distal end of the tubular braiding, forming a proximal disk of the proximal end of the tubular braiding, forming a central aperture in each of the distal and proximal discs such that said apertures are joined by a central channel of the tubular braiding, extending between said discs, and fixating the opposite ends of wire in a connecting element located at the proximal disk with an off-set distance from a central axis extending through the channel.

Some embodiments of the disclosure provide for retaining the size of the shunt, and thereby the desired blood flow.

Some embodiments of the disclosure provide for improved anchoring of the device, while maintaining a high flexibility to adapt to various geometries.

Some embodiments of the disclosure provide for an improved stability of the device.

Some embodiments of the disclosure provide for reduced risk of formation of emboli.

It should be emphasized that the term "comprises/comprising" when used in this specification is taken to specify the presence of stated features, integers, steps or components but does not preclude the presence or addition of one or more other features, integers, steps, components or groups thereof.

BRIEF DESCRIPTION OF THE DRAWINGS

These and other aspects, features and advantages of which embodiments of the disclosure are capable of will be apparent and elucidated from the following description of embodiments of the present disclosure, reference being made to the accompanying drawings, in which;

FIG. 4d is a cross-sectional view;

DESCRIPTION OF EMBODIMENTS

Figure 1A:
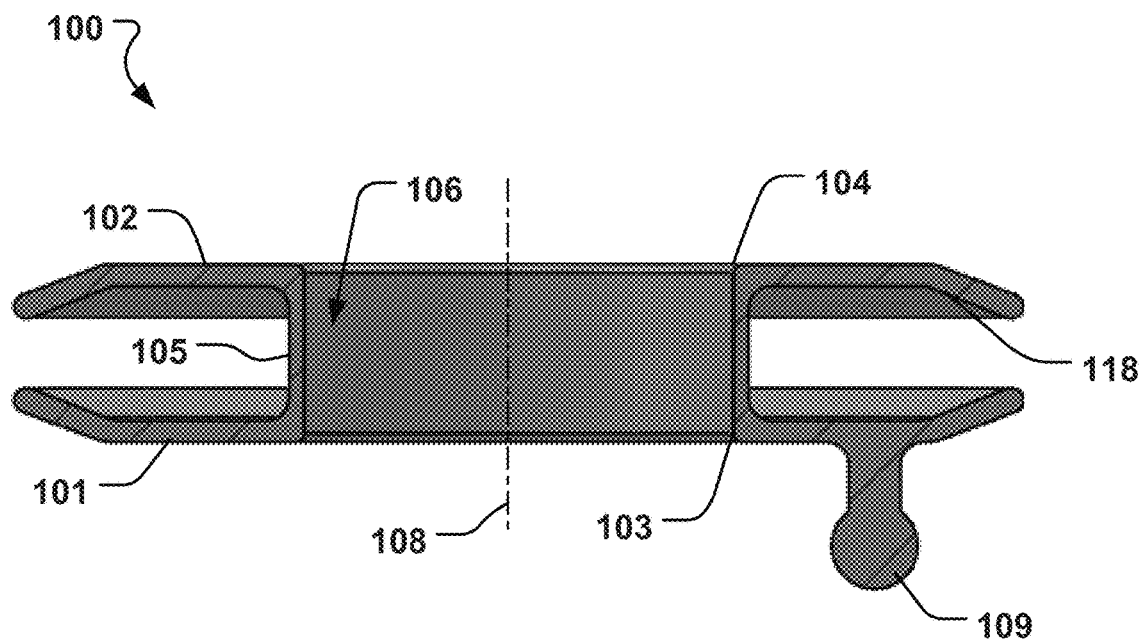
FIGS. 1a-b illustrate a blood flow regulator according to embodiments of the invention in a top-down view of the distal disc and in side view, respectively.

Specific embodiments of the disclosure now will be described with reference to the accompanying drawings. This disclosure may, however, be embodied in many different forms and should not be construed as limited to the embodiments set forth herein; rather, these embodiments are provided so that this disclosure will be thorough and complete, and will fully convey the scope of the disclosure to those skilled in the art. The terminology used in the detailed description of the embodiments illustrated in the accompanying drawings is not intended to be limiting of the disclosure. In the drawings, like numbers refer to like elements The following description focuses on embodiments of the present disclosure applicable to blood regulating devices for septal defects. However, it will be appreciated that the disclosure is not limited to this application but may be applied to many other medical implants including for example stents, vascular devices, and various other devices that can be provided with a well-defined shunt such as a Patent foramen ovale (PFO) device, a PDA device, or a ventricular septal defect (VSD) device.

Figure 1B:
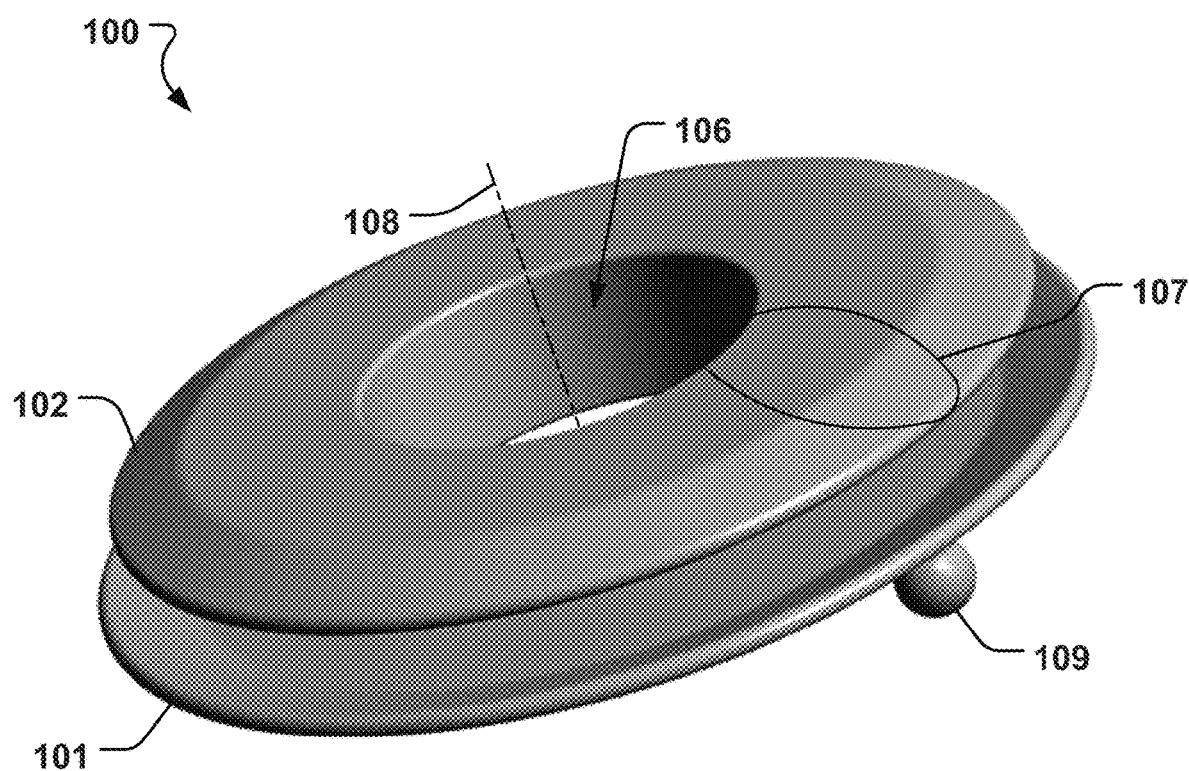
Figure 2A:
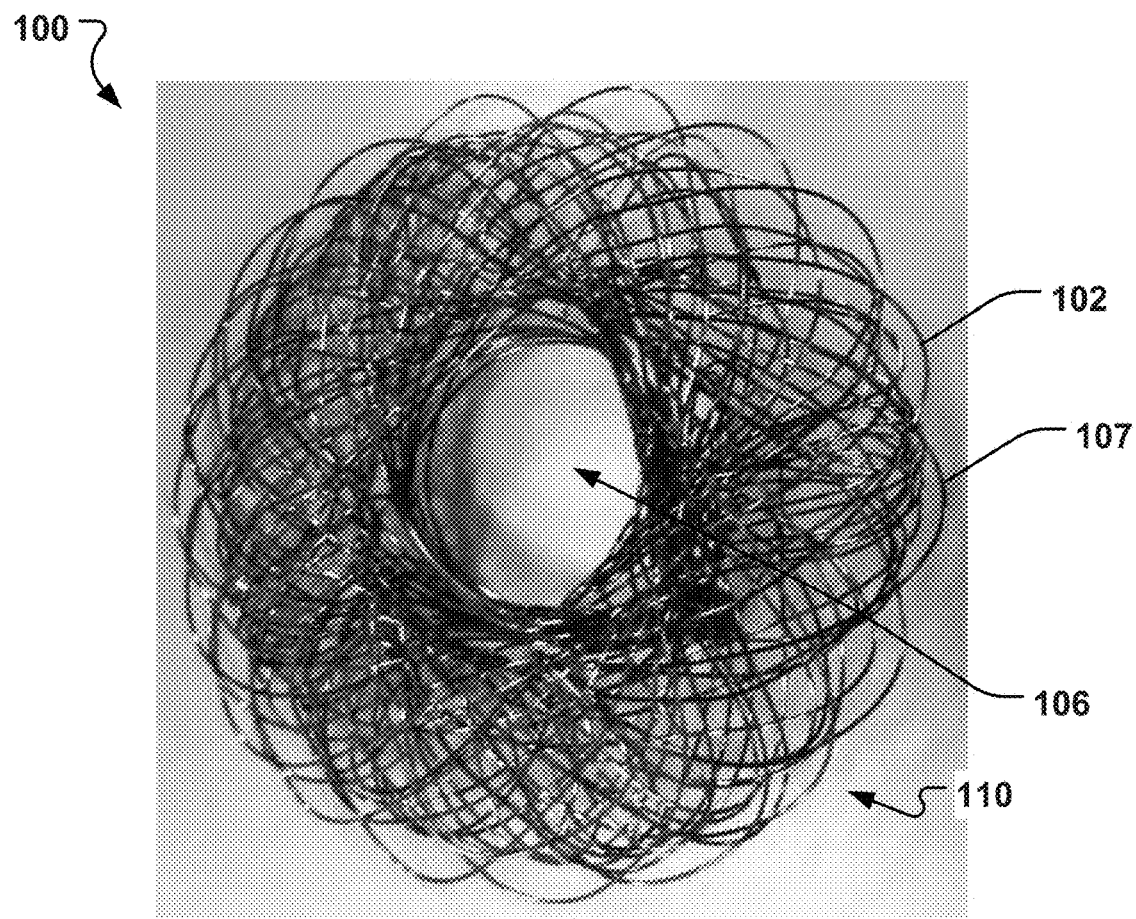
FIGS. 2a-b illustrate a blood flow regulator according to embodiments of the invention in a top-down view of the distal disc and in side view, respectively.

FIG. 1a is a blood flow regulator 100 for creating a shunt in the heart, comprising a proximal element 101 having a general disc-shape, defined by a braid of one or more wires extending about a central aperture 103 of the proximal element. The blood flow regulator further comprise a distal element 102 having a general disc-shape, defined by a braid of one or more wires extending about a central aperture 104 of the distal element, and a third element 105 defining a neck section intermediate the proximal and distal elements and forming a cavity 106, i.e. a trough hole or channel extending through the proximal element, the distal element and the third element. The proximal and distal elements are placed on either side of the septum, with the third element 105 situated within the septum. The diameter of the cavity 106 is not greater than the diameter of each of the distal and proximal elements 101, 102. The distal element 102 comprises at least one loop 107 of a wire extending radially outwardly from a center 108 of the distal element 102 and returning towards said center 108 of the distal element 102. I.e. the braiding of the distal element 102 comprises wires that extend radially outward, i.e. radiates out to a perimeter, from the center axis 108, and then returning towards the center axis 108, thereby forming a loop wire 107. FIG. 1b illustrates only schematically an example of such loop wire 107. FIG. 1a illustrates the blood flow regulator device in a cross-sectional side view. This advantageously removes the need of having to collect wire ends at the distal element of the blood flow regulator 100. A problem with prior art devices is that any element at the distal end collecting the wire ends, such as a connector, weld, or hub, presents a discontinuity in the braiding which will create less than optimal conditions for the endothelialization process, and even result in formation of embolies. Distal connectors will in some instances even protrude from the distal element and thereby further disrupt the endothelialization process. Thus, the wire loops 107 of the braiding at the distal element 102 will provide for a smooth, even, and continuous distal surface that allows for optimal conditions for formation of endothelia. In some embodiments of the invention, all of the wires forming the distal element 102 are loop wires 107, thus the distal element 102 is free from wire ends, that will provide for the smooth, even, and continuous distal surface with the advantages described previously. FIG. 2a shows a top-down view of the distal element or disc 102 of blood flow regulator device 100, showing the loop wires 107 having their apex at the peripheral region of the distal disc 102. In this embodiment, also all of the wires forming the braiding of the distal element are loop wires 107, whereby the distal element is free from wire ends.

The proximal element 101, the distal element 102, and the third element 105 may be formed of the same braiding of one or more wires. Thus the blood flow regulator device 100 may be formed from the same single piece of braiding, which is illustrated in e.g. FIGS. 2a-b, and 3a-b. This provides for a flexible device that adapts well to the anatomy, after expanding out of the delivery catheter, while at the same time providing good fixation at the implanted site and the necessary support for keeping an open channel, and further, less manufacturing steps. The device 100 can flatten, fold, or collapse inside of delivery catheter and the respective elements of the device recover their original shape after removal from catheter.

The device 100 may comprise one or more radiopaque markers (not shown) in order to identify the device 100 during the procedure. The radiopaque marker can be applied to any part of the device. The marker may be applied at the periphery of the aperture 103 or 104, so that the channel 106 can be clearly localized. It may be desired to access the opening 106 with a catheter.

Figure 2B:
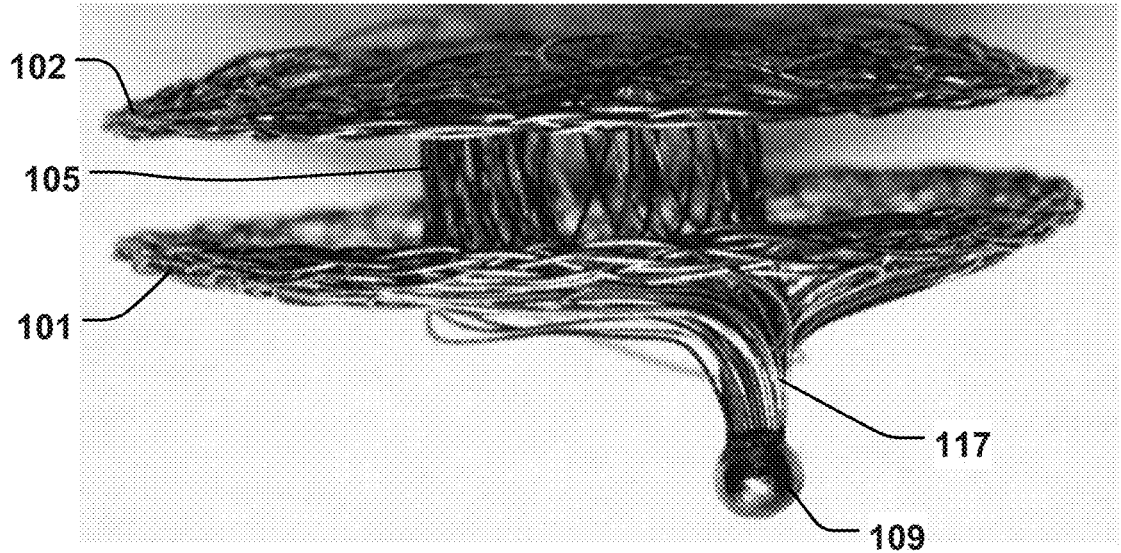
Figure 3A:
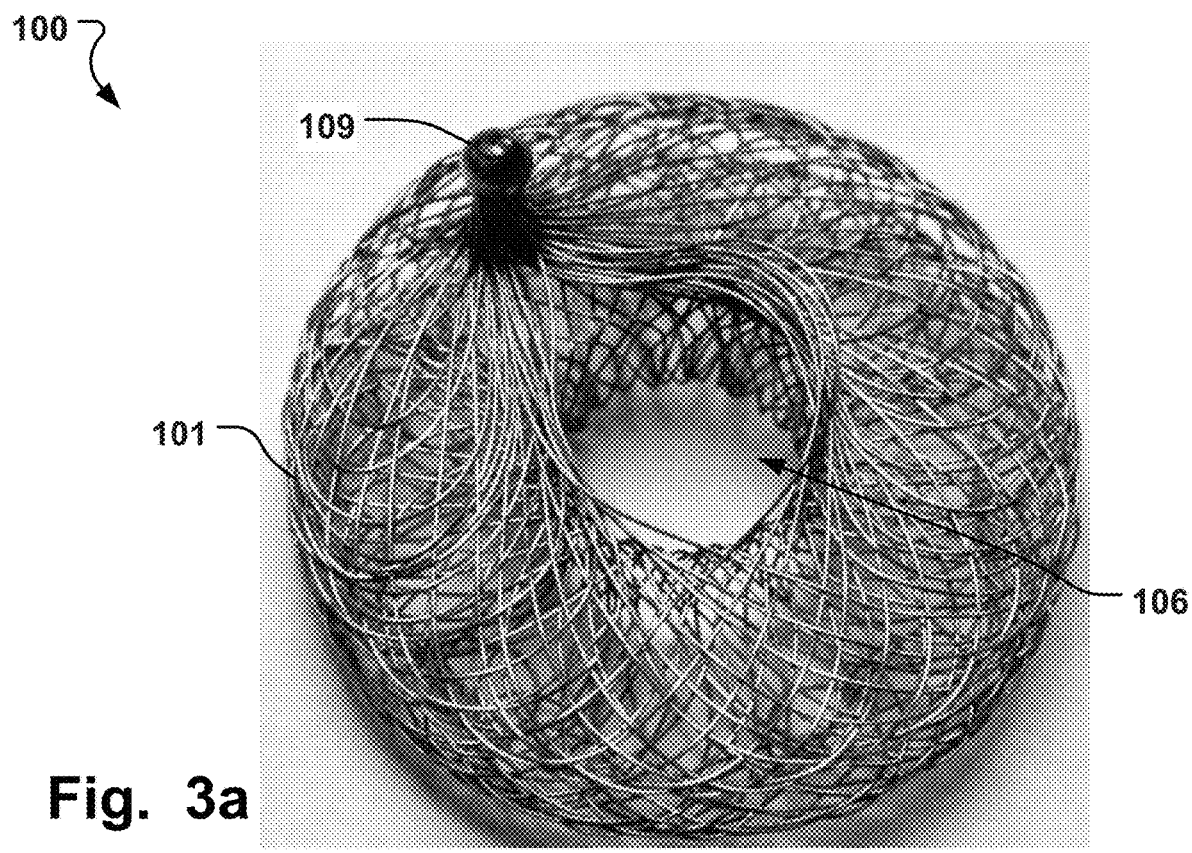
FIGS. 3a-b illustrate a blood flow regulator according to embodiments of the invention in a top-down view of the proximal disc and distal disc, respectively.

The proximal element may comprise a connecting element 109 for a delivery device, wherein ends of the one or more wires are fixed to the connecting element. The distal element 102 comprises returning loops 107 of the one or more wires whereby opposite ends of the one or more wires forming the distal element 102 are fixed to the connecting element 109. Thus, the ends of the wires forming the distal element 102 are fixated to the connecting element 109 at the proximal end 101. FIG. 2b, which is a side-view, and FIG. 3a, which is a view of the proximal end 101, illustrates how the ends of the wires are fixated to the connecting element 109, and there is no other connecting element present, or wire end that is not terminating in the proximal connecting element 109. The distal element 102 can therefore be formed of the wire loops 107 and present a flat and smooth surface with the advantages discussed above. Having a smooth, continuous distal surface, which requires fixation of all wire ends to a single proximal connecting element 109, while simultaneously having the connecting element 109 arranged with an off-set distance 119, allowing for the a through channel 106 across the device 100, is advantageously provided and possible due to having the wires at the proximal end 101 looped around the central aperture 103 as illustrated in FIG. 3a.

Figure 3B:
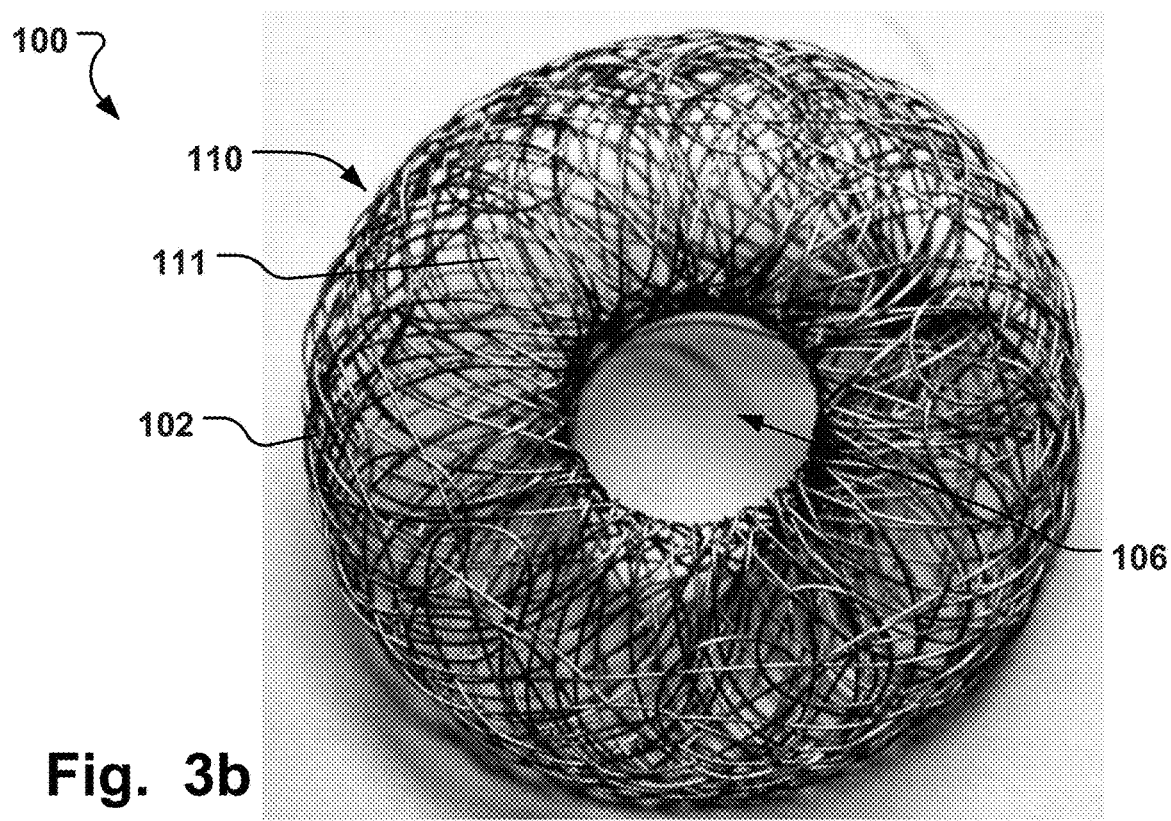
Figure 4A:
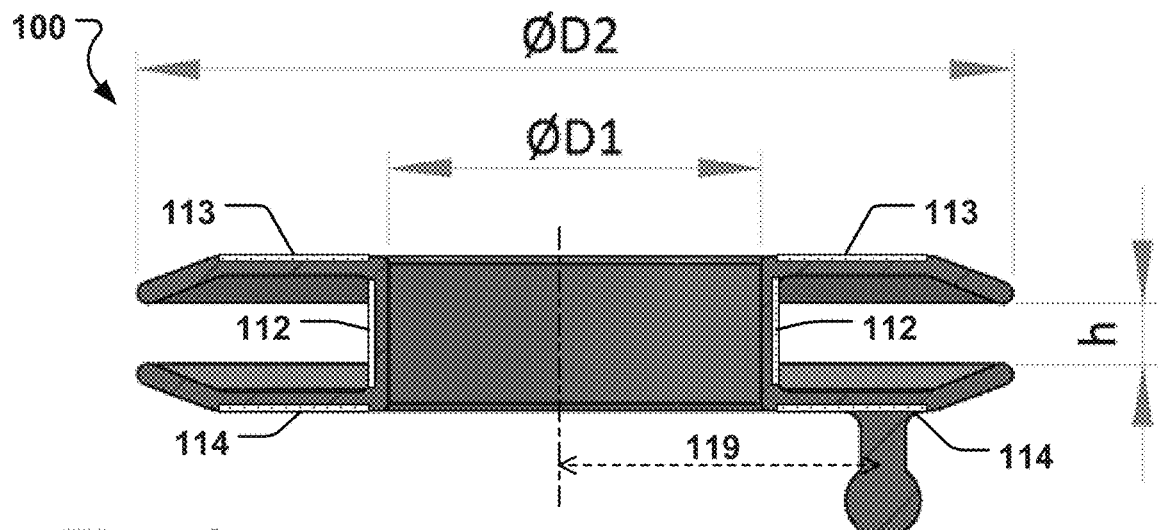
FIGS. 4a-b illustrate a blood flow regulator according to embodiments of the invention in a cross-sectional side view and in a perspective view of the proximal disc, respectively.
Figure 4B:
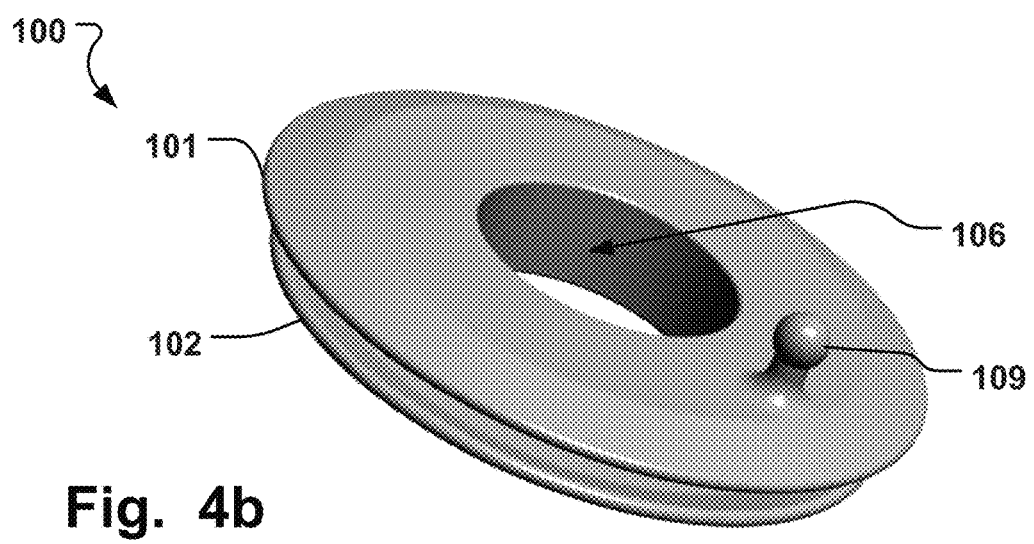
Figure 4C:
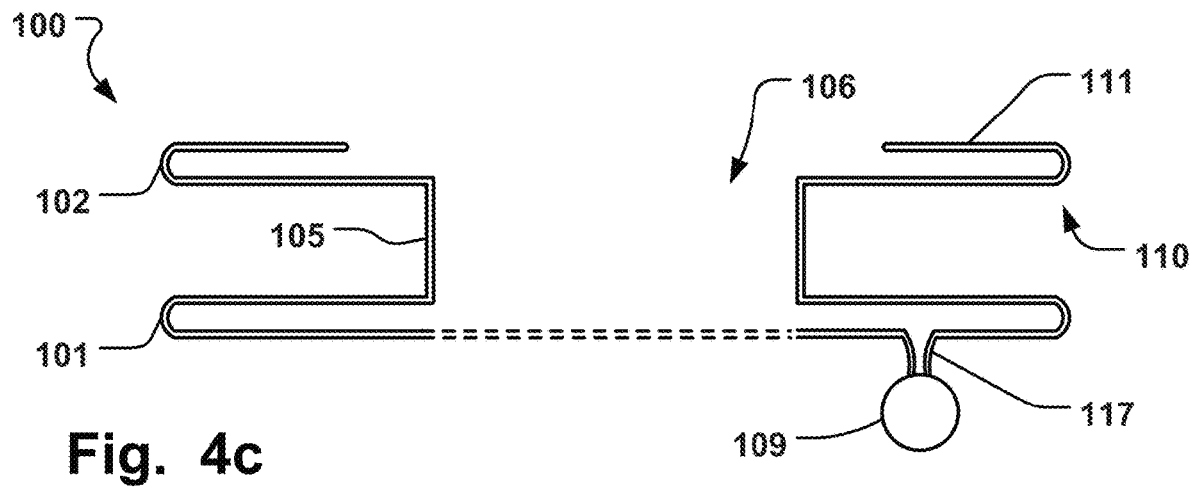
FIG. 4c illustrates a blood flow regulator according to an embodiment of the invention in a schematic cross-sectional side view of the outline of the braiding.

The braiding at a perimeter 110 of the distal element 102 may be folded radially inwards to form a double layer 111 braid around the perimeter 110 of the distal element 102, which is illustrated schematically in FIG. 4c. Like the proximal element 101, the distal element 102 may thus have a double layer of braiding around a peripheral portion thereof. The fold 111 may extend with a length radially inwards towards the center axis 108 as desired. The perimeter 110 of the distal disc can thus be provided with a more even circular shape, e.g. comparing FIG. 2a which is not folded with FIG. 3b which has the folded braiding, which can be advantageous with respect to the handling of the device and also the behavior of the device when implanted, as the fold 111 can further increase the structural integrity of the device 100.

The blood flow regulator 100 may further comprise a membrane 112 arranged around the cavity or channel 106, which is illustrated in FIG. 4a. The membrane 112 can prevent ingrowth of tissue in the cavity 106, thus providing for maintaining the desired flow for long-term use. The membrane can be provided on the outside or the inside of the third element 105. The membrane can be applied by coating a polymer fiber on the third element 105. The polymer fiber can be applied by a spin coating process, where the device 100 can be rotated while spraying the polymer fiber onto the device 100.

Figure 8A:
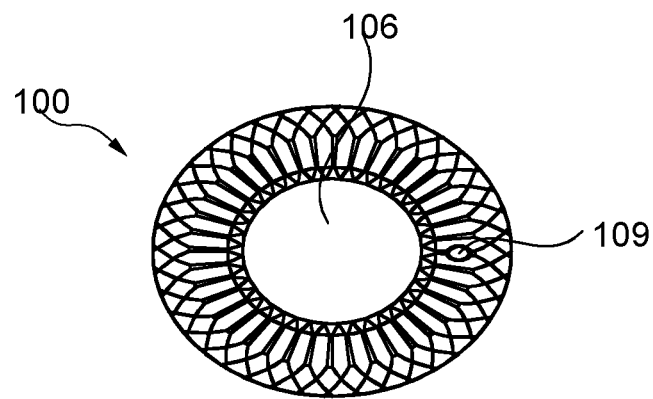
FIGS. 8a-c illustrate a blood flow regulator according to embodiments of the invention in a top-down plan view, a cross-sectional side view, and in a perspective side view, respectively.

The distal element 102 may further comprise of a membrane 113 that promotes endothelialization. In addition, or alternatively, the proximal element 101 may further comprises of membrane 114 that promotes endothelialization. FIG. 4a illustrates how the membranes, 112, 113, 114, may be arranged on the blood flow regulator 100, but the membrane coverage in the device 100 may be varied as desired for the application. FIGS. 6b and 8a also illustrate a membrane arranged at the proximal element, but may also be positioned at the distal element.

Figure 6A:
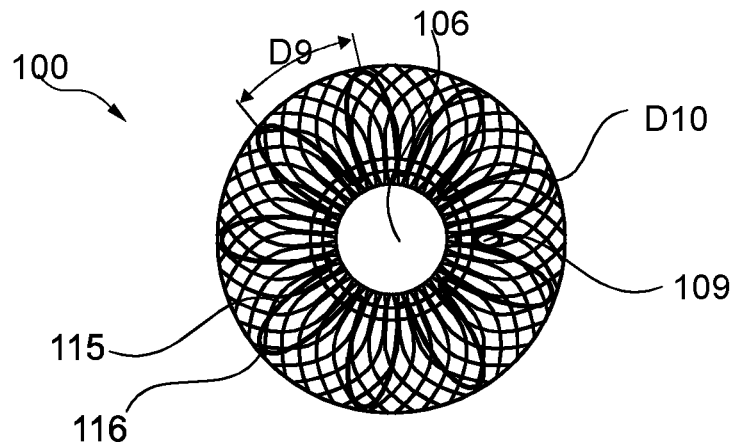
FIGS. 6a-c illustrate a blood flow regulator according to embodiments of the invention in a top-down plan view, a cross-sectional side view, and in a perspective side view, respectively.
Figure 6B:
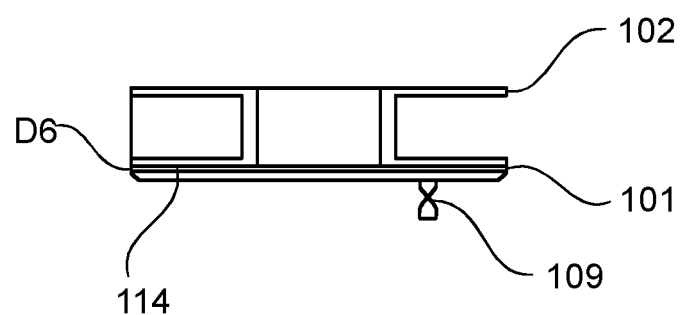
Figure 6C:
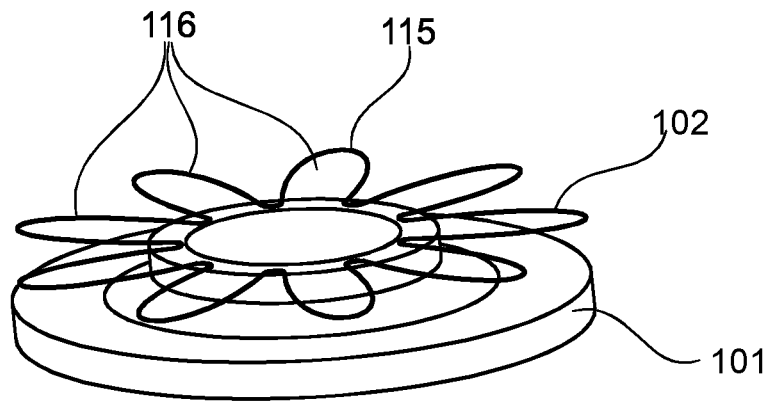

The distal element 102 may comprise non-braided filaments 115 forming petal-shaped loops 116, which is illustrated in FIGS. 6*a-c*.

The flow control device illustrated in FIGS. 6*a-c* is thus partly braided and has comparatively less amount of metallic structure than the previously described examples in FIGS. 1-4. Having less metal may facilitate the incorporation the device in the body since the tissue overgrowth can be faster. The non-braided filaments may have a different rigidity or flexibility which may be advantageous in some applications. The strength of disc-shaped region of distal element 102 does not affect the strength of the proximal element 101.

The device 100 in FIGS. 6*a-c* is designed to create a shunt between vessels and heart chambers while minimizing metallic structure and facilitating calibration of a diagnostic system. The filament body structure 115 of the distal element 101 may be formed of one or more nitinol filaments, or any other metal alloy that is biocompatible, and being able to heat set in the desired shape. It may be advantageous to have at least three filaments 115, which can be equally spaced apart to achieve the desired stability of the device 100.

The retention force of the distal element 102 can be adjusted by selecting the number of filaments 115.

The distal element 102 may be formed from a single filament wire or it can be formed from a plurality of filament wires.

A desired filament body structure may employ, for example, 3, 4, 5, 12 6, 7, 8, 9, 10, or 12 pieces of filaments as desired depending on the use of the device. All these filaments may have a regular or irregular filament body structure, e.g. forming forming a petal shape as mentioned, where each filament 115 extend from the axial center 108 of a geometric plane, and each filaments joining each other in a radially inward location, e.g. by welding. The filament body structure may be obtained using techniques such as pinching sutures or wires together or hooking sutures or wires together.

The filaments 115 may be of equal gauge or of different gauge (wire size).

The distal element 102 and the proximal element 101 may be formed separately and combined prior to implantation. The third element 105, may also be formed separately.

It is possible to manufacture the proximal and distal elements with completely different properties independently.

It is also possible that the proximal element 101 is formed from non-braided filament wires 115, which can assume a petal-shaped proximal portion.

In a method, the different parts can be joined using techniques such as welding, pinching, clamping or hooking a plurality of wires together.

It is also possible that a braided device 100, having a braided proximal 101 and distal 102 element and a third neck portion 105 is combined with non-braided filament wires 115.

Further, the proximal and distal elements 101, 102, may be braided with different wire thicknesses, which would allow e.g. different expansion forces of the proximal and distal elements 101, 102, such as when having a non-braided distal element 102.

The proximal and distal elements 101, 102, are expandable, and the proximal element may thus have a lower expansion strength than the distal element.

The third element 105 may be resilient such that it is deformable to a non-circular shape in a septum of the heart, such as to an at least partly oval shape or any irregular shape.

In general the device 100 has elastic properties making it suitable both systolic and diastolic motion of the septum, in particular the atrial septum. The third element 105 may be flexible to allow movement of the proximal and distal elements 101, 102, relative to each other, in the plane of the disc-shaped elements, i.e. a parallel sliding motion. This is advantageous in some irregular-shaped anatomies. Further the third element 105 may movement in the axial direction, along the centre axis 108, which allows for a certain adaptation to the geometry of the anatomy also in this direction.

The third element 105 may have an at least partly oval cross-section in the relaxed, unstrained, heat-set shape. This may be advantageous in some anatomies, and the device can more easily adapt to the anatomy without producing unnecessary strain or dislocation. The cavity 106 may thus also be formed as desired, e.g. having the oval cross-section. The proximal and distal elements 101, 102, may also have varying shapes, such as oval or other irregular shapes as may be advantageous for varying anatomies, and not only disc-shaped. The oval or irregular shapes of the mentioned elements are formed in the heat-setting procedure with respectively shaped molds, such that the shapes can be maintained.

The connecting element 109 may be joined to the proximal portion 101 via a flexing element 117 formed from the one or more wires being fixated to the connecting element, as illustrated in e.g. FIGS. 2*b* and 4*c*. This allows for a flexibility between the connecting element 109 and the proximal and distal portions 101, 102 of the device 100, which can be advantageous during the implantation procedure, e.g. in narrow anatomies where the angle between the delivery device and the blood flow regulating device 100 needs to be increased at the implantation stage, and the pivoting motion provided by the connecting element itself may not be sufficient.

The connecting element 109 may be formed by a weld having an at least partly spherical shape, as illustrated in e.g. FIG. 2*b*. This allows for the mentioned pivoting motion by grasping the connecting element with a delivery device having a holder with the corresponding spherical surface.

The distal element 102 may comprise an at least partly concave shape 118 being concave in a direction towards the proximal element 101, which is illustrated in e.g. FIGS. 1*a* and 2*b*. This facilitates a flush apposition of the distal element 102 against the tissue, and also improved fixation, since the concave surface forms an angled rim at the periphery of the distal disc that may flex against the tissue, thereby creating a bias force against the tissue in the axial direction 108. The proximal element may also have a concave shape towards the distal element 102, as illustrated in FIG. 1*a*. FIG. 4*a* illustrates the case where the distal element 102 and the proximal element 101 are generally parallel to each other. It may however be possible to have varying angles between these elements.

The central apertures 103, 104, may be arranged concentrically in the proximal and distal elements 101, 102, respectively, as illustrated in e.g. FIG. 3*b*. Such symmetry may be advantageous with respect to structural stability of the device 100 and may provide for a more secure anchoring of the device 100 at the implanted site since the disc portions of the proximal and distal ends has a uniform overlap with the tissue.

The membrane 113 of the distal element, and/or the membrane 114 of the proximal element may be formed of a thin, flexible material and comprise at least one of; a partially biodegradable material; a filament; an elastic polymeric material; or one or more natural fabrics such as silk or wool can be used.

In one embodiment, the membrane 113, 114, is formed of a woven polyester. The membrane 113, 114, may be made of a dense material. Membranes 113, 114, can also be made, at least partly, by a biodegradable material, which also facilitate thrombosis.

The membrane 113, 114, may comprise an elastic polymeric material selected from a group including nylon, polyester, polypropylene, polytetrafluoroethylene, and expanded polytetrafluoroethylene.

In one embodiment, at least one of the distal element 102 or the proximal element 101 includes a coating, preferably a cell proliferation coating. The use of a cell proliferation coating enhances the adhesion and proliferation of endothelial cells onto surfaces. The use of similar coatings may further provide faster endothelization.

Figure 4D:
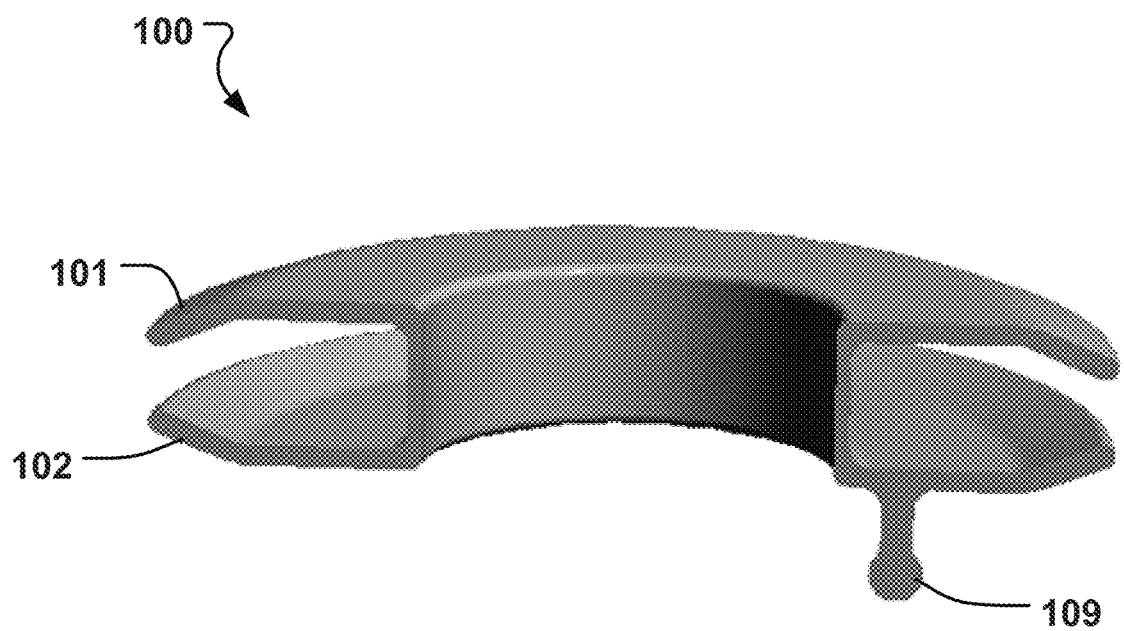
FIGS. 4d-e illustrate a blood flow regulator according to an embodiment of the invention in further perspective views, where
Figure 4E:
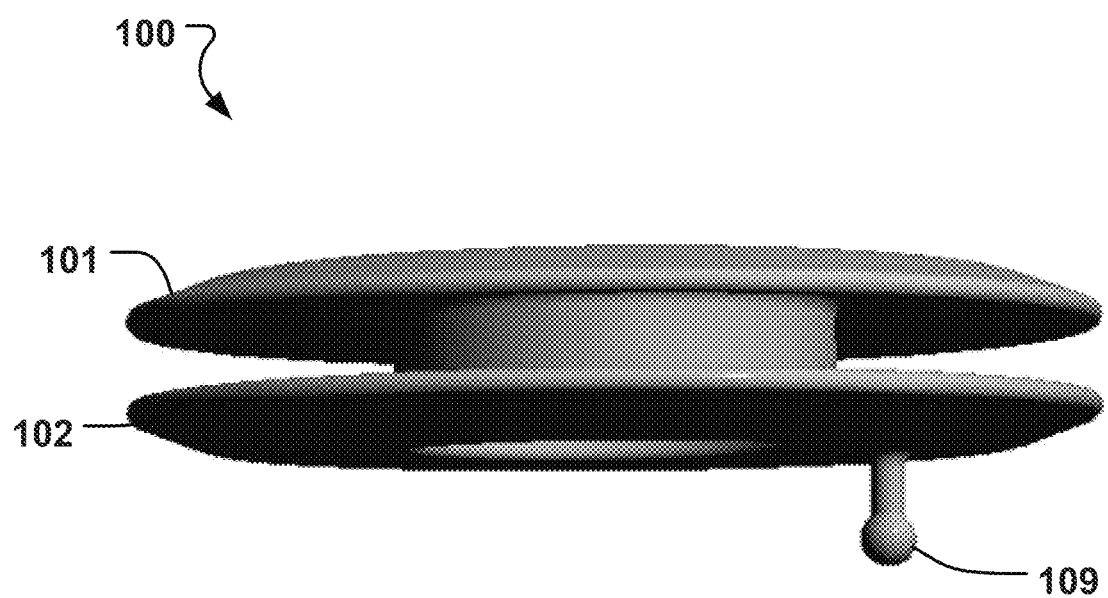

Table 1 and FIG. 4a show possible dimensions of the outer diameter D2 of the distal and/or proximal elements, as well as the diameter D1 of the cavity 106, and the closest distance (h) between the proximal and distal elements 101, 102. The dimensions are given for respective puncture size. In FIGS. 4a, 4d, 4e, the proximal and distal discs have similar or same diameter, but the diameters of these discs may be different and varied as desired for the application. E.g. FIG. 4b illustrates a larger proximal disc. Alternatively, the distal disc may be larger than the proximal disc.

TABLE 1

| Puncture Size | D1 [mm] | D2 [mm] | h [mm] | Introducing System Size ODS* |
|---|---|---|---|---|
| D ≤ 4 | 4 | 17 | 2 | 8F |
| 5 < D ≤ 6 | 6 | 19 | 2 | 10F |
| 6.5 < D ≤ 8 | 8 | 22 | 2 | 12F |
| 7.5 < D ≤ 10 | 10 | 24 | 2 | 14F |
| D ≤ 4 | 4 | 17 | 5 | 8F |
| 5 < D ≤ 6 | 6 | 19 | 5 | 10F |
| 6.5 < D ≤ 8 | 8 | 22 | 5 | 12F |
| 7.5 < D ≤ 10 | 10 | 24 | 5 | 14F |
| D ≤ 4 | 4 | 17 | 10 | 8F |
| 5 < D ≤ 6 | 6 | 19 | 10 | 10F |
| 6.5 < D ≤ 8 | 8 | 22 | 10 | 12F |
| 7.5 < D ≤ 10 | 10 | 24 | 10 | 14F |

Figure 5A:
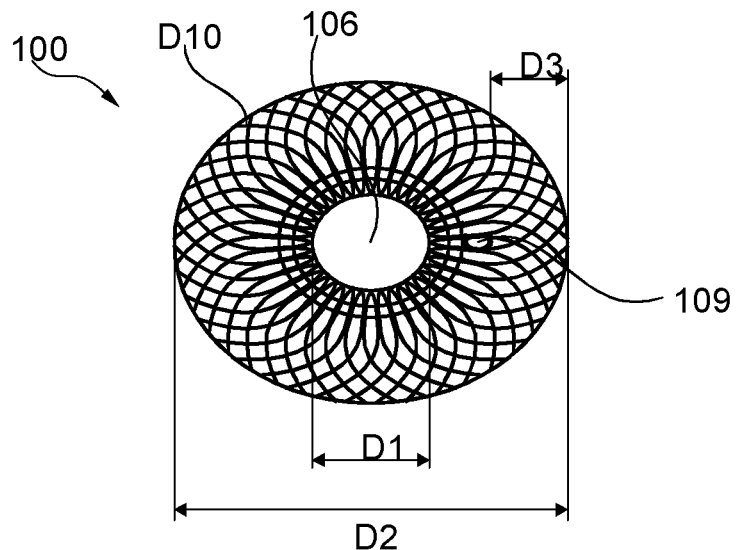
FIGS. 5a-c illustrate a blood flow regulator according to embodiments of the invention in a top-down plan view, a cross-sectional side view, and in a perspective side view, respectively.
Figure 5B:
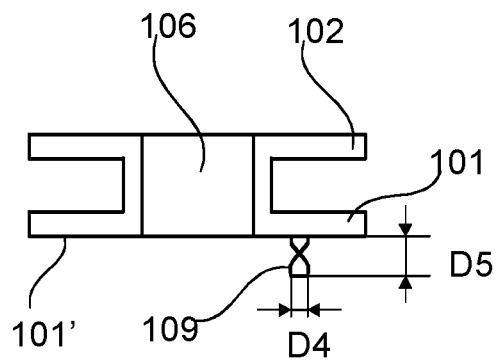
Figure 5C:
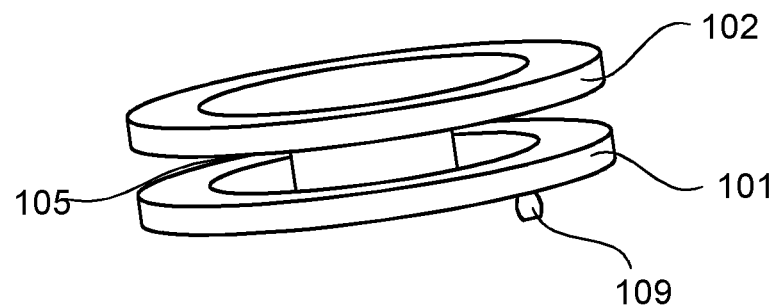
Figure 7A:
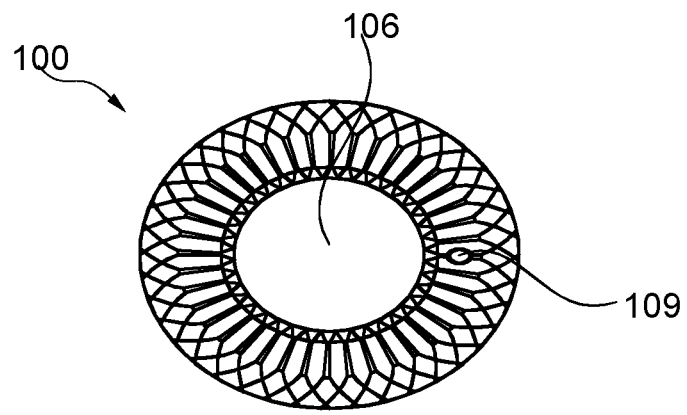
FIGS. 7a-c illustrate a blood flow regulator according to embodiments of the invention in a top-down plan view, a cross-sectional side view, and in a perspective side view, respectively.
Figure 7B:
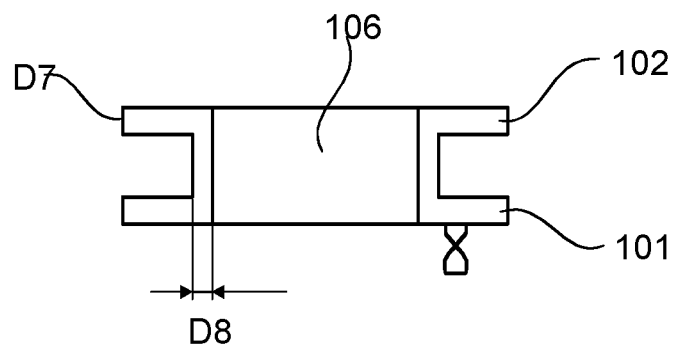
Figure 7C:
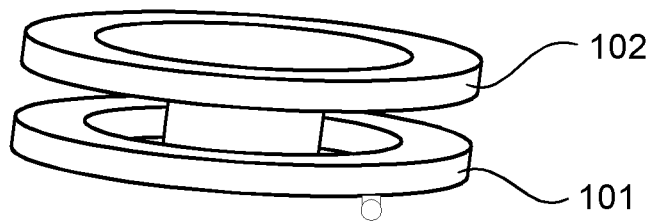
Figure 8B:
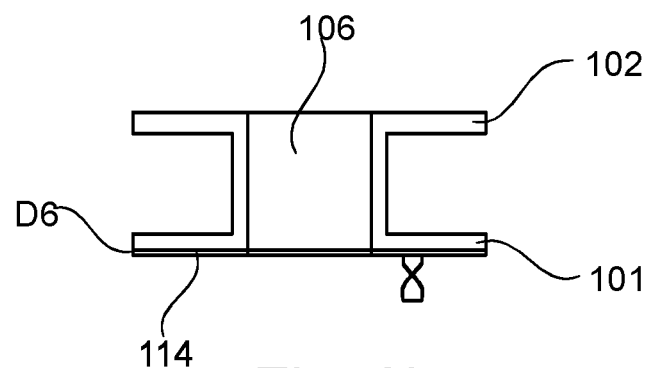
Figure 8C:
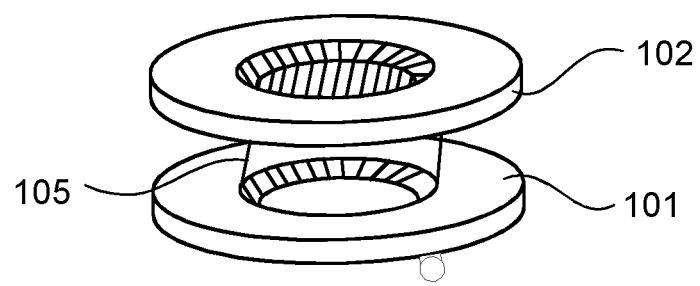

FIGS. 5a-c, 6a-c, 7a-c, and 8a-c are other illustrations of the blood flow regulating device 100 described above. Diameters D1 and D2 are indicated in FIG. 5a. D1 may be varied to provide the desired flow in the shunt, while D2 is varied to provide sufficient anchoring of the device at the septum. Further dimensions of the device 100 are discussed with reference to FIGS. 6a-c, 7a-c, and 8a-c. For example, with reference to FIG. 6a, dimension D9 is an angular distance between crests of two adjacent nitinol filaments (loops) 115, which are formed to create the distal unit 102 of the flow control device 100. Dimension D10 is intended as a reference to nitinol wire diameter, which may vary according to device size. Turning to FIG. 5b, dimension D4 is the diameter of a connecting element 109 used to connect the flow control device to a pusher cable of a catheter used for device implantation. Dimension D5 is a distance between a proximal element surface 101' of the proximal element 101 and the connecting element 109. As illustrated in FIG. 6b, for example, dimension D6 is the thickness of the membrane 114 on the proximal element 101 of the flow control device 100. The thickness of the membrane 113 on the distal element 102 is not indicated, but the thickness of the both membranes can be equal. Turning to FIG. 7b, dimension D8 is the thickness of the frame between the cavity diameter D1 and the waist diameter of the third element 105. As illustrated in FIG. 5a, dimension D3 is the distance between the outer tangent of the flow control device diameter and the center of the connecting element 109. FIGS. 7a-c illustrate a flow control device 100 having a cavity 106 with a larger diameter than e.g. the device 100 illustrated in FIGS. 5a-c and 6a-c, thus used for providing a larger opening. FIGS. 8a-c illustrate a flow control device 100, which is used to create a hole in a body with a longer connecting neck, i.e. having a longer dimension (h), for different applications such as posterior descending artery (PDA) stenting. Generally, the two discs on the two sides of the device provide maximum support with a clamping force and with a very limited distance between the disc, providing for improved anchoring and stabilization of the device after implantation, and maintaining the calibrated size of the channel.

Figure 10:
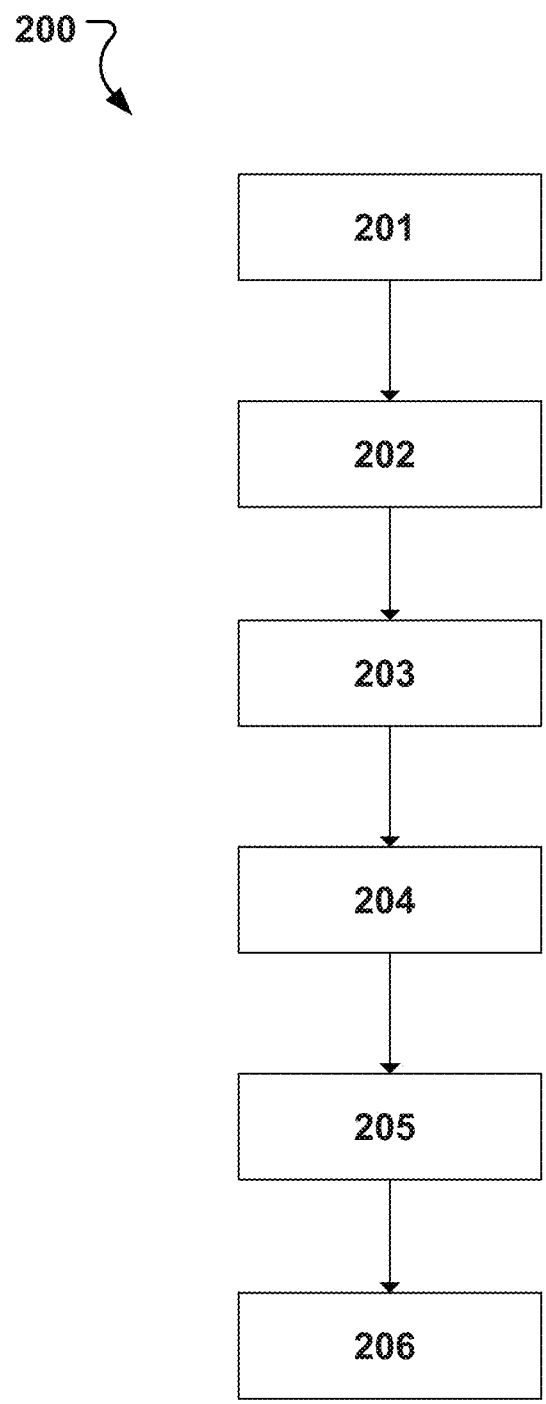
FIG. 10 is a flow-chart of a method of manufacturing a blood flow regulator according to embodiments of the invention.

FIG. 10 illustrates a method 200 of manufacturing a blood flow regulator 100. The method comprises braiding 201 a tubular braid of wires, where opposite ends of each wire are arranged at a proximal portion of the tubular braid, and loops of the wires are arranged at a distal end of the tubular braiding. The method comprises forming 202 a distal disc 102 of the distal end of the tubular braiding, forming 203 a proximal disk 101 of the proximal end of the tubular braiding. The method 200 further comprises forming 204 a central aperture 103, 104, in each of the distal and proximal discs such that the apertures are joined by a central channel 106 of the tubular braiding, extending between the discs, and fixating 205 the opposite ends of wire in a connecting element 109 located at the proximal disk with an off-set distance 119 from a central axis 108 extending through the channel. The off-set distance 119 is illustrated in FIG. 4a, and may be varied as desired for providing the optimal location of the connecting element 109.

The method 200 may further comprise folding 206 the braiding at a perimeter 110 of the distal element 102 radially inwards to form a double layered braid 111 around the perimeter 110 of the distal element 102.

The various flow control device 100 of the present disclosure are used in medical procedures to provide a shunt in the body, such as in an atrial septum. The medical procedure in question may also comprises of following steps. Positioning the flow control device with a restraining catheter. Positioning a pushing cable into the restraining catheter adjacent to the device. Inserting the restraining catheter, the pushing cable, and the device into the body at a transdermal site. Positioning the distal end of the restraining catheter at the target site and the device inside the body opening created by a previous interventional method such as septostomy.

Figure 9:
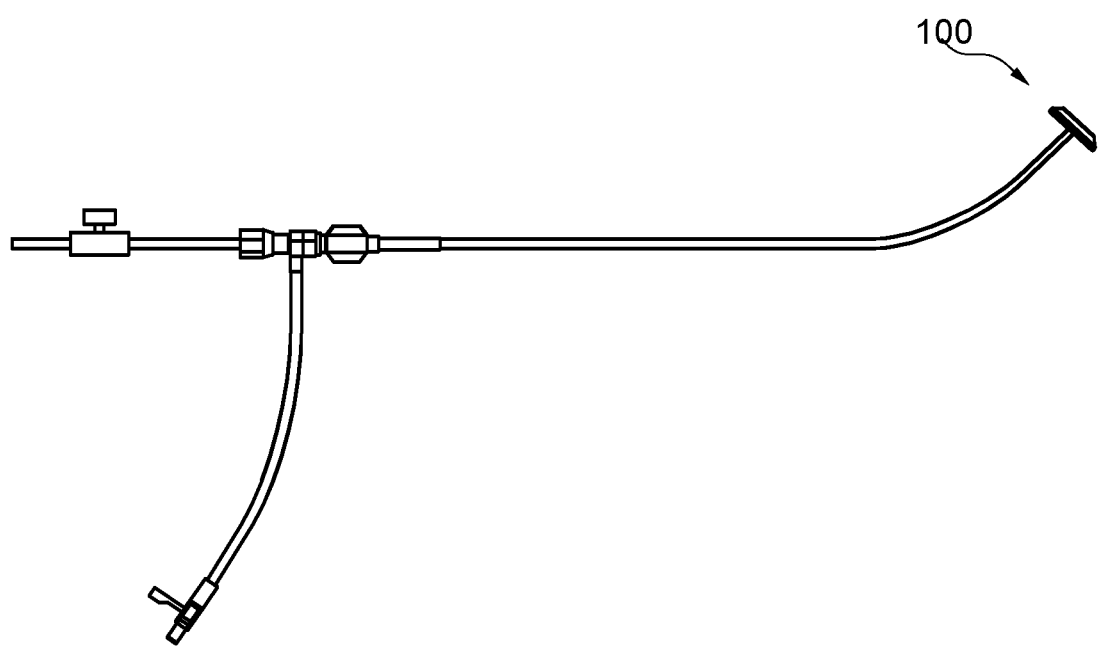
FIG. 9 illustrate a catheter used for implantation of a blood flow regulator according to embodiments of the invention.

Pushing the device through the restraining catheter with the pushing cable until the device has been released, so that distal element of the device is positioned on an inside of a rupture. Removing the pushing cable and the retraining catheter, so that distal part of the distal unit of the device is positioned on an inside of a rupture to be shaped by the device. FIG. 9 shows a lateral view of a catheter suitable for use in the above described medical procedure for closure of a hole in a body. The catheter is used to deliver the flow control device, also referred to as the blood flow regulating device 100, to the desired location and perform a precise implantation. In one exemplary use, a delivery sheath is placed in the punctured hole in the arterial septum with the aid of a guide wire. The pusher cable with a plastic torque control is used to advance the flow control device to the desired location and to deploy the flow control device when it is advanced to the right location.

The present disclosure has been described above with reference to specific embodiments. However, other embodiments than the above described are equally possible within the scope of the disclosure. Different method steps than those described above, may be provided within the scope of the disclosure. The different features and steps of the disclosure may be combined in other combinations than those described. The scope of the disclosure is only limited by the appended patent claims. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present disclosure is/are used.

What is claimed is:

1. A method of shunting a heart comprising:
   providing a braided flow control device having a disc-shaped proximal element, a disc-shaped distal element, a neck section therebetween and no more than one connecting element, said one connecting element disposed on said proximal element;
   delivering said braided flow control device through a catheter to a rupture in a wall of a heart chamber;
   urging force against said one connecting element to deploy said braided flow control device until said disc-shaped distal element and said disc-shaped proximal element are positioned on either side of said rupture in said wall of a heart chamber
   allowing said braided flow control device to thereby control blood flow across said rupture of said heart.

2. A method according to claim 1, wherein urging force against said one connecting element comprises urging force against a plurality of wires that make up said braided flow control device, said plurality of wires terminating at said connecting element.

3. A method according to claim 1, wherein urging force against said one connecting element comprises urging force against a spherically shaped connecting element.

4. A method according to claim 1, further comprising puncturing a hole in said wall of a heart chamber to create said rupture.

5. A method according to claim 1, wherein said wall of a heart chamber is an atrial septum.

6. A method according to claim 1, wherein urging force against said one connecting element comprises pushing against a cable in contact with said one connecting element.

7. A method of affecting blood flow in a heart comprising:
   providing a flow control device having a proximal element, a distal element, a neck section therebetween and no more than one connecting element, said one connecting element disposed on said proximal element;
   delivering said flow control device through a catheter to a rupture in a wall of a heart chamber;
   urging force against said one connecting element to deploy said flow control device until said distal element and said proximal element are positioned on either side of said rupture in said wall of a heart chamber
   allowing said braided flow control device to thereby control blood flow across said rupture of said heart.

8. A method according to claim 7, wherein said distal and proximal elements are disc-shaped.

9. A method according to claim 7, wherein said flow control device is comprised of a plurality of wires that originate and terminate at said one connecting element.

10. A method according to claim 7, wherein urging force against said one connecting element comprises urging force against a plurality of wires that make up said flow control device, said plurality of wires originating and terminating at said connecting element.

11. A method according to claim 7, wherein urging force against said one connecting element comprises urging force against a spherically shaped connecting element.

12. A method according to claim 7, further comprising puncturing a hole in said wall of a heart chamber to create said rupture.

13. A method according to claim 7, wherein said wall of a heart chamber is an atrial septum.

14. A method according to claim 7, wherein urging force against said one connecting element comprises pushing against a cable in contact with said one connecting element.

* * * * *